United States Patent [19]

Barnish et al.

[11] 4,341,792
[45] Jul. 27, 1982

[54] HETEROBICYCLIC KETO- AND AMINO-ACIDS, ESTERS AND AMIDES

[75] Inventors: Ian T. Barnish, Ramsgate; Peter E. Cross, Canterbury, both of England

[73] Assignee: Pfizer Inc., New York, N.Y.

[21] Appl. No.: 280,862

[22] Filed: Jul. 6, 1981

Related U.S. Application Data

[63] Continuation-in-part of Ser. No. 187,431, Sep. 15, 1980, abandoned.

[30] Foreign Application Priority Data

Sep. 15, 1979 [GB] United Kingdom ................. 7932049

[51] Int. Cl.³ .................... A61K 31/34; A61K 31/35; C07D 307/84; C07D 311/041
[52] U.S. Cl. .................................. 424/275; 424/283; 424/285; 549/23; 549/57; 549/58; 549/398; 549/405; 549/406; 549/462; 549/471
[58] Field of Search ...................... 260/346.22, 346.73, 260/345.2; 424/275, 283, 285; 549/23, 57, 58

[56] References Cited

U.S. PATENT DOCUMENTS 4,029,811  6/1977  Tamagnone et al. .............. 424/285
4,138,397  2/1979  Bohme ............................ 260/239.1
4,148,920  4/1979  Barnish et al. ..................... 424/319

OTHER PUBLICATIONS

Chatelus, Ann. Chim., 4, 505–547, (1949); Chem. Abstr., 44, 1975c, (1950).
European Patent Appln. 8, 752 Publ. Mar. 19, 1980; Derwent Abstracts, 20590c/12 (1980).
Chatelus et al., Comptes Rendus, 224, 1777–1779, (1947).

Primary Examiner—Richard Raymond
Attorney, Agent, or Firm—Connolly and Hutz

[57] ABSTRACT

Heterobicyclic glyoxylic acids, L- and DL-heterobicyclic glycines and their derivatives of the formulae

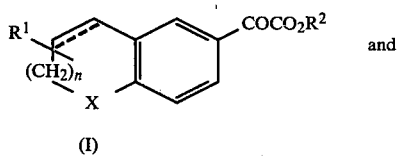

and

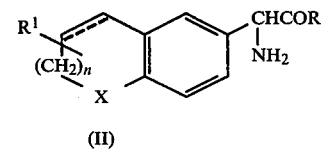

and pharmaceutically acceptable cationic and acid addition salts thereof, wherein R is $OR^2$ or $NHR^3$;

$R^2$ is hydrogen or alkyl having from one to four carbon atoms;

$R^3$ is hydrogen, alkyl having from one to four carbon atoms, alkoxyalkyl having from one to four carbon atoms in each of the alkyl groups or $R^4R^5C_6H_3CH_2$— where $R^4$ and $R^5$ are H, OH, F, Cl, Br, I, or alkyl or alkoxy having from one to four carbon atoms $R^1$ is hydrogen, alkyl having from one to four carbon atoms or $R^4R^5C_6H_3$—; X is oxygen or sulfur; n is 0 or 1 and the broken line represents an optionally present double bond; useful in treatment of diseases and conditions which are characterized by reduced blood flow, reduced oxygen availability or reduced carbohydrate metabolism in the cardiovascular system.

39 Claims, No Drawings

HETEROBICYCLIC KETO- AND AMINO-ACIDS, ESTERS AND AMIDES

CROSS-REFERENCE TO RELATED APPLICATION

This is a continuation-in-part of co-pending application Ser. No. 187,431, filed Sept. 15, 1980, now abandoned.

BACKGROUND OF THE INVENTION

1. Field of the Invention

The invention relates to certain heterobicyclic keto- and amino-acids, esters and amides of the formulae (I) and (II) as defined herein and pharmaceutically acceptable salts thereof, pharmaceutical compositions thereof and their use in treating diseases and conditions of mammalian subjects, including humans, which are characterized by reduced blood flow, reduced oxygen availability or reduced carbohydrate metabolism in the cardiovascular system of the subject; such conditions include ischaemic heart disease (particularly angina pectoris and myocardial infarction) and cardiac failure. The compounds are also useful in treating diseases involving defects in carbohydrate metabolism such as diabetes.

2. Description of the Prior Art

Chatelus, Ann. Chim., 4, 505–47 (1949); Chem. Abstr., 44, 1975c (1950); Comptes Rendus, 224, 1777–79 (1947) records the preparation of 2,3-dihydrobenzofuranglyoxylic acid and its ethyl ester; and ethyl 6-chromanylglyoxylic acid.

U.S. Pat. No. 4,029,811 and European patent application No. 8,742, published Mar. 19, 1980 disclose acylation of 2-ethylchroman and 2-ethyl-2,3-dihydrobenzofuran with ethyl chloroglyoxalate and aluminum chloride to provide the corresponding 2-ethyl-6-chromanylglyoxalate and 2-ethyl-2,3-dihydro-5-benzofuranglyoxalate esters, useful as chemical intermediates.

U.S. Pat. No. 4,138,397 discloses 2,3-dihydro-5-benzofuranylglycine useful as an intermediate in production of 6-[2-amino-(2,3-dihydro-5-benzofuranyl)acetamido]-penicillin and derivatives.

The prior art does not disclose any medical use for the compounds of the instant invention, nor has any use been proposed for them, except as chemical intermediates.

In U.S. Pat. No. 4,148,920 L- and DL-phenylglycines of the formula

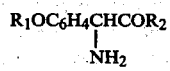

where $R_1$ is hydrogen or methyl and $R_2$ is $NH_2$, OH or completes a carboxylic ester group are disclosed as useful in treating diseases and conditions characterized by reduced blood flow, oxygen availability or reduced carbohydrate metabolism in the cardiovascular system. The D-isomers are disclosed as inactive.

SUMMARY OF THE INVENTION

The present invention provides novel benzofurans, benzothiophenes, chromenes (also referred to herein as 2H-1-benzopyrans), thiachromenes (also referred to herein as 2H-1-benzothiopyrans), and dihydro-analogs thereof of formula

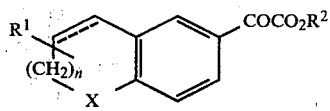

and the corresponding L- and DL-glycine derivatives of the formula

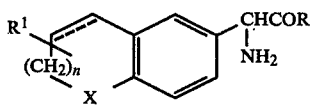

and their pharmaceutically acceptable cationic and acid addition salts.

In the compounds of formula (I) and pharmaceutical compositions containing them, $R^1$ is hydrogen, alkyl having from one to four carbon atoms or

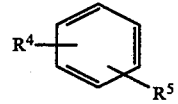

where $R^4$ and $R^5$ are the same or different and are each a member selected from the group consisting of H, OH, F, Cl, Br, I and alkyl and alkoxy having from one to four carbon atoms; $R^2$ is hydrogen or alkyl having from one to four carbon atoms; X is oxygen or sulfur, n is 0 or 1 and the broken line is a bond or no bond; with the proviso that when X is oxygen and the broken line is no bond, $R^1$ is limited to $-C_6H_3R^4R^5$; and pharmaceutically acceptable cationic salts thereof.

Pharmaceutically acceptable cationic salts of the compounds of formula (I) include, e.g., pharmaceutically acceptable metal, ammonium and amine salts of the carboxylic acid of formula (I).

Pharmaceutically acceptable metal salts include, e.g., the sodium, potassium and calcium salts. Pharmaceutically acceptable amine salts include, e.g., salts with arginine, N-methylglucamine and choline.

The compounds of formula (II) are pharmaceutically acceptable bioprecursors of the corresponding glyoxylate compounds of formula (I), without the proviso stated above. By pharmaceutically acceptable bioprecursor is meant a compound having a structural formula different from formula (I) but which, upon administration, is converted in the patient's body to a compound of formula (I), as defined above, but without the proviso.

In the compounds of formula (II) and pharmaceutically acceptable cationic and acid addition salts thereof, R is $OR^2$ or $NHR^3$ where $R^2$ is as defined for compounds of formula (I), above and $R^3$ is a member selected from the group consisting of hydrogen, alkyl having from one to four carbon atoms, alkoxyalkyl having from one to four carbon atoms in each of the alkyl groups and

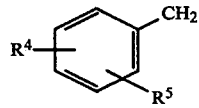

where $R^4$ and $R^5$ are as defined above; X, n, the broken line and $R^1$ are as defined above for compounds of formula (I), but with the proviso that when X is oxygen, n is 0 and the broken line is no bond, R is limited to $NHR^3$. The compounds and salts of formula (II) are active by virtue of their metabolism in vivo to produce a corresponding compound of the formula

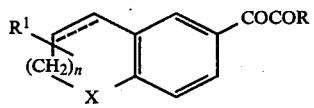
(IA)

where R is $OR^2$ or $NHR^3$ as defined above.

The amides of formula (II), where R is $NHR^3$, in particular, have advantages in use because of their better solubility properties. They have been found to be surprisingly more soluble than their carboxylic acid or ester counterparts in aqueous media at a pH in the range of from about 5–8, i.e., at pH's most often encountered in physiological systems.

Compounds of formula (II) wherein R is hydroxy form cationic salts including the pharmaceutically acceptable metal, ammonium and amine salts defined above.

Pharmaceutically acceptable salts of compounds of the formula (II) include addition salts with acids containing pharmaceutically acceptable anions, e.g., the hydrochloride, the hydrobromide, sulphate or bisulphate, phosphate or acid phosphate, acetate, maleate, fumarate, succinate, lactate, tartrate, citrate, gluconate, saccharate and p-toluenesulfonate salts.

The glycine derivatives of formula (II) each have a chiral center at the carbon atom bearing the amino group. With regard to these compounds, the L-form is the preferred form, the D-form being substantially inactive. It will therefore be appreciated that the L-isomers of formula (II) will be substantially more active than the corresponding DL-(racemic) compounds.

The compounds of formulae (I) and (II) in which the broken line is no bond and $R^1$ is other than hydrogen also have a chiral center at the $R^1$-bearing carbon atom. The invention includes those compounds of formulae (I) and (II) wherein this chiral center is racemic and each of the resolved isomers.

Also provided are pharmaceutical compositions comprising a pharmaceutically acceptable carrier and a cardiovascular blood flow, oxygen availability or carbohydrate metabolism increasing amount of a compound of formula (I) or (II) as defined above, or a pharmaceutically acceptable salt thereof.

The invention further provides a method of treating mammalian subjects, including humans, suffering from a disease or condition attributable to reduced blood flow, reduced oxygen availability or reduced carbohydrate metabolism in the cardiovascular system which comprises parenterally administering to said subject a cardiovascular blood flow, oxygen availability or carbohydrate metabolism increasing amount of a compound of formula (I) without proviso, (II) without proviso, or a pharmaceutically acceptable salt thereof.

Preferred compounds of formula (I), because of their high activity in tests, are those wherein $R^2$ is hydrogen and $R^1$ is hydrogen, methyl or phenyl. Particularly preferred are such compounds wherein:

(a) the broken line is no bond and: $R^1$ is H, n=0 and X is oxygen or sulfur; or $R^1$ is H, n=1 and X is oxygen; and (b) those wherein the broken line is a bond and $R^1$ is H, 2-methyl or 2-phenyl; n=0 and X is oxygen.

Preferred compounds of formula (II), because of their solubility in aqueous systems and high level of activity, are those wherein R is $NHR^3$ and $R^1$ is hydrogen, methyl or phenyl. Particularly preferred are such compounds wherein:

(a) the broken line is no bond and: $R^1$ is H, n=0; X is oxygen and $R^3$ is H or $CH_2CH_2OCH_3$; and (b) those compounds wherein the broken line is a bond, $R^1$ is H, n=0, X is oxygen and $R^3$ is H or $CH_2CH_2OCH_3$.

Especially preferred compounds of the invention include:

DL-2-amino-2-[2,3-dihydro-5-benzo(b)furanyl]-acetamide and

DL-N-(2-methoxyethyl)-2-amino-2-(2,3-dihydro-5-benzo(b)furanyl)acetamide.

DETAILED DESCRIPTION OF THE INVENTION

The compounds of the invention may be prepared by a number of different routes including the following: (1) Compounds of the formula (I) wherein $R^2$ is hydrogen or alkyl having from one to four carbon atoms and the optional double bond is absent, may be prepared by reacting a compound of the formula:

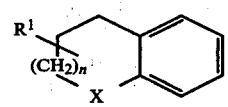
(III)

wherein $R^1$, n and X are as previously defined, with a alkyl oxalyl chloride, having one to four carbons in the alkyl group, in the presence of a Friedel-Crafts catalyst, e.g. aluminum chloride, to give corresponding compounds of the formula (I) wherein $R^2$ is $C_1$–$C_4$ alkyl, and, if desired, hydrolysis to yield the corresponding acids where $R^2$ is hydrogen.

This reaction is generally performed with the compound of formula (III) and the alkyl oxalyl chloride ($R^2OCOCOCl$) dissolved in a reaction-inert organic solvent, e.g. 1,2-dichloroethane or dichloromethane. The Friedel-Crafts catalyst, usually aluminum chloride in powdered form, is then added and the mixture stirred at room temperature for several hours. The product is isolated in a conventional manner, e.g. by pouring the reaction mixture into aqueous acid, separating the organic layer, drying and evaporating the solvent. The crude product may be further purified, if desired, by recrystallization or by distillation as appropriate.

The hydrolysis step to yield the acids of formula (I) where $R^2$ is hydrogen is performed in an entirely conventional manner, for example by treating the ester where $R^2$ is said alkyl, with an alkali-metal base, e.g. sodium or potassium hydroxide. The reaction is conveniently achieved by warming a mixture of the ester and the aqueous alkali on a steam bath and is usually complete within several hours under these conditions. The product may be isolated as the salt, e.g. the sodium or potassium salt or alternatively the solution is acidified with an acid e.g. hydrochloric acid and the product is isolated as the free acid, e.g. by solvent extraction and evaporation of the solvent.

The starting materials of the formula (III) are readily available from commercial sources or they may be prepared by literature routes from readily available starting materials. For reviews on methods of preparation of 2,3-dihydrobenzofurans, 2,3-dihydrobenzothiophenes (thionaphthenes), chromans and thiochromans see, e.g., Elderfield, "Heterocyclic Compounds", Vol. 2, J. Wiley and Sons, Inc., New York, 1951; Mustafa in "The Chemistry of Heterocyclic Compounds", edited by Weissburger et al., Vol. 29, J. Wiley and Sons, Inc., New York, 1974; Schneller in "Advances in Heterocyclic Chemistry", Vol. 18, edited by Katritzky et al., Academic Press, New York, 1975, pp. 59–97 and Cagniant, ibid., p. 337–473. For example, two generally useful methods are outlined below.

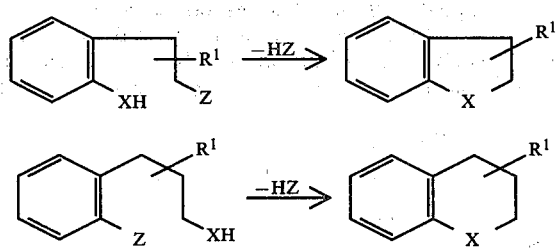

where $R^1$ and X are as defined above and Z is Cl, Br, OH or SH. The reactions are carried out under cyclizing conditions, e.g. by heating in the presence of polyphosphoric acid or sulfuric acid. (2) Compounds of the formula (II) wherein R is $OR^2$ or $NHR^3$ where $R^2$ and $R^3$ are as previously defined and the optional double bond is absent, may be prepared by reacting a compound of the formula (III) (as previously defined) with an α-hydroxy-amino acid of the formula:

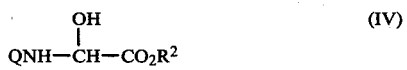

where $R^2$ is as previously defined and Q is a conventional acid-stable amino protecting group to give a compound of the formula:

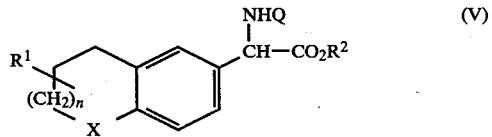

The protecting group is subsequently removed to yield the compounds of formula (II) wherein R is $OR^2$ or alternatively, in the case where $R^2$ is hydrogen, the product is reacted with ammonia or an amine of the formula $R^3NH_2$ (where $R^3$ is as previously defined but is other than hydrogen) and the protecting group Q is removed to yield the compounds of formula (II) wherein R is $NHR^3$.

The reaction of the compound of the formula (III) and the α-hydroxy-amino acid of formula (IV) is acid catalysed and is generally achieved by adding the compound of formula (III) to a solution of the compound of formula (IV) in an organic solvent containing a strong acid. For example, the reaction may be carried out in glacial acetic acid containing concentrated sulphuric acid as the catalyst, or in toluene in the presence of p-toluenesulfonic acid. The reaction is conveniently performed at room temperature and is generally substantially complete after several hours, e.g. an overnight period. The reaction mixture is worked up in a conventional manner, e.g. by pouring the mixture into water and ice which generally induces the product to solidify and it may then be collected by filtration and further purified, if desired, by recrystallization.

The protecting group Q needs to be chosen having regard to the above reaction conditions, i.e. it must be reasonably stable under acidic conditions. Suitable protecting groups are the benzyloxycarbonyl, the benzoyl, the acetyl and chloroacetyl groups, the benzyloxycarbonyl group being generally preferred because of its ease of removal. For example, the benzyloxycarbonyl group may be removed by hydrogenolysis, generally achieved by exposing a solution of the N-protected product to a stream of hydrogen gas in the presence of a noblemetal catalyst, e.g. palladium-on-charcoal, at room temperature for 4–6 hours. The product is then isolated, after filtration, by evaporation of the solvent. Alternatively, the benzyloxycarbonyl group may be removed with a solution of hydrogen bromide in glacial acetic acid. In this latter case the free amino acid of formula (II) wherein R is OH is isolated as the hydrobromide salt by precipitation with diethyl ether or following evaporation of the solvent.

The benzoyl, acetyl or chloroacetyl groups are removed by alkaline hydrlysis, e.g. by heating with 5 N aqueous sodium hydroxide on a steam bath for several hours.

The amides of formula (II) wherein the optional double bond is absent and R is $NHR^3$ were $R^3$ is as previously defined, are obtained via the N-protected compound of formula (V) wherein $R^2$ is hydrogen by reaction with ammonia or with an amine of the formula $R^3NH_2$ (where $R^3$ is as previously defined other than hydrogen). This reaction is generally performed in the presence of a coupling or activating agent. Thus, for example, the amine may be reacted with the acid of formula (V) in the presence of dicyclohexylcarbodiimide, or an activated ester may be prepared, e.g., the N-hydroxysuccinimide ester may be prepared by reacting the acid with N-hydroxysuccinimide and dicyclohexylcarbodiimide. Alternatively, an anhydride or mixed-anhydride derivative of the acid may be prepared, e.g., by reaction of the acid in a suitable solvent (e.g., tetrahydrofuran) with a chloroformate, e.g., isobutylchloroformate, in the presence of a base, e.g., triethylamine, at a low temperature, e.g., −10° to +10° C. for several minutes. Ammonia, as a saturated ethanolic solution, or the amine of formula $R^3NH_2$ (where $R^3$ is other than hydrogen) is then added, generally, in a slight excess, and the reaction mixture is stirred for one or two hours at room temperature. The product is isolated in a conventional manner, for example by solvent extraction, washing to remove unreacted starting materials and removal of the solvent. The N-protecting group is then finally removed as previously described to yield the amide products of formula (II) wherein R is $NHR^3$. The products may be further purified, is desired, by recrystallization or by chromatography. In an alternative process the amides of formula (II) where R is $NH_2$ may be obtained from the esters of formula (II), particularly those wherein $R^2$ is methyl or ethyl, by reaction with concentrated ammonia solution at room temperature for several hours (typically overnight).

The esters may be obtained from the acids of formula (II) by a conventional esterification reaction, e.g., using thionyl chloride in methanol or ethanol. Acid addition salts may be prepared from the amino compounds of formula (II) in a conventional manner, e.g., by mixing solutions containing equimolar proportions of the compound of formula (II) and the appropriate pharmaceutically acceptable acid. The product which generally precipitates from solution is collected by filtration or otherwise by evaporation of the solvent.

The α-hydroxy amino acid derivatives of formula (IV) are generally known compounds or they may be prepared by conventional methods from readily accessible starting materials. Thus, N-benzyloxycarbonyl-α-hydroxy-glycine is described in Tetrahedron, 31, 863 (1975). Other N-protected derivatives may be prepared by analogous methods. Esters may be prepared from the acids by conventional esterification reactions, e.g., by an acid catalyzed esterification with the desired alkanol.

(3) Compounds of the formulae (I) and (II) wherein the optional double bond is present are prepared from a nitrile (VI) according to the following scheme:

tion is performed in a reaction inert organic solvent, e.g., tetrahydrofuran, and is generally achieved by adding a small molar excess (e.g., a 10% excess) of sodium hydride in finely divided form to a solution of methyl methylthiomethyl sulphoxide. The nitrile (VI) is then added, generally using an equimolar amount dissolved in the same solvent, and the reaction mixture is then warmed, e.g., at 50°–60° C., for a period of several hours until the reaction is substantially complete. The product (VII) is isolated in a conventional manner, e.g., by the addition of water, solvent extraction and evaporation of the dried solvent. The product may be reacted with cupric chloride to give the keto esters of formula (VIII) or alternatively converted to the amino acids of formula (XII).

The reaction to give the keto esters of formula (VIII) is achieved by reacting the enamino sulphoxide intermediate (VII) with cupric chloride in the presence of a lower aliphatic alkanol. The reaction is generally performed by stirring equimolar amounts of the reactants in excess alkanol, e.g., ethanol, as solvent. The reaction is conveniently performed at room temperature and

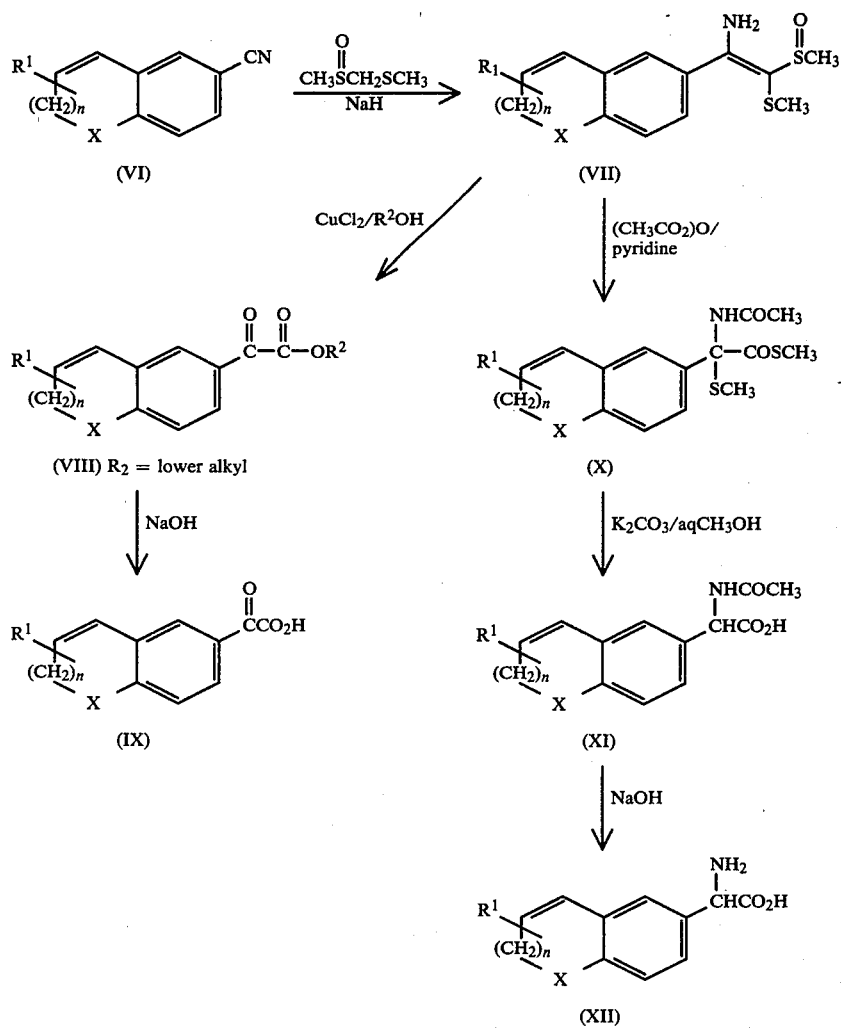

The route is based on the procedure recently published by Ogura, et al., Tetrahedron Letters, 375, (1978). Thus as a first step, the nitrile (VI) is reacted with methyl methylthiomethyl sulphoxide and sodium hydride to give the enamino sulphoxide (VII). This reaction generally requires a period of several days to go to completion under these conditions. The product is isolated in a conventional manner, e.g., by filtration, solvent extraction, washing with water and evaporation of the dried solvent. The ester (VIII) wherein R² is as defined above may be readily converted to the glyoxylic acid (IX) wherein R² is hydrogen by a conventional alkaline hydrolysis, e.g., by warming with dilute sodium hydroxide for an hour or so.

As an alternative, the intermediate (VII) is treated with acetic anhydride and the product heated with potassium carbonate in aqueous methanol to give the N-acetyl glycine derivative (XI). The reaction with acetic anhydride is generally performed by adding acetic anhydride to a solution of the enamino sulphoxide (VII) dissolved in a reaction inert organic solvent, e.g., dichloro methane in the presence of an organic base, e.g., pyridine. A small molar excess, e.g., a 50% excess of acetic anhydride is generally employed and the reaction is conveniently performed by stirring the reaction mixture at room temperature for several hours. The product is isolated by removal of the solvents and solvent extraction of the crude product. The product is dissolved in aqueous potassium carbonate and heated under refulx for several hours. The glycine derivative (XI) may then be isolated, after washing the aqueous phase with an organic solvent, by acidifying the reaction mixture with e.g., hydrochloric acid. The product which separates from solution in solid form may be collected by filtration and further purified, if desired, by recrystallization. The N-acetyl group is finally removed in an entirely conventional manner, e.g., by heating with aqueous sodium hydroxide for a period of several hours. The glycine (XII) is obtained by acidification to pH 5-6 and may be collected by filtration and dried.

The amino acid (XII) may be converted to the amide or ester of formula (II) as defined above by entirely conventional reactions. Thus, the acid (XII) may be reacted with thionyl chloride in a lower alkanol to give the ester which is then treated with concentrated aqueous ammonia solution to give the amide product. Alternatively, the amino group may be protected with a conventional amino protecting group and the carboxyl group reacted with an amine R³NH₂ (where R³ is as previously defined other than hydrogen) using an activating or coupling agent, e.g., dicyclohexylcarbodiimide. The carboxyl group may also be esterified by conventional techniques. The protecting group is finally removed using conditions appropriate to the particular protecting group employed. Such reactions are entirely conventional and conditions for their performance will be well known to those skilled in the art.

The nitriles of formula (VI) are in some cases known compounds or they may be prepared by analogous and well known chemical processes. Thus, 2-methyl-5-cyanobenzo(b)-furan is described by Mooradian and Dupont in J. *Heterocyclic Chem.*, 4, 441 (1967). The 2-phenylderivative may be prepared from acetophenone oxime by a similar sequence of reactions as shown below.

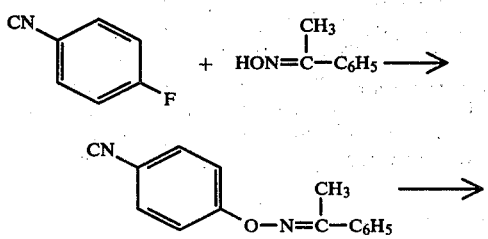

-continued

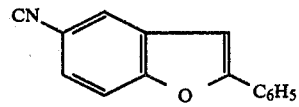

5-Cyanobenzo(b)furan itself is readily available from the 5-bromo compound by reaction with cuprous cyanide. Preparation of 6-cyano-2H-benzopyran and its 2-methyl derivative (where n=B 1), has been described by Harfenist and Thom in J. Org. Chem., 37, 841 (1972). Alternatively, the compounds of formula (VI) are obtained from the corresponding 5-amino (n=0) or 6-amino (n=1) derivatives by diazotization in the presence of cyanide ion, the well-known Sandmeyer Reaction.

In each of the above routes (1), (2) or (3), the products of formulae (I) or (II) having an acidic or basic grouping may be isolated as the free acid or its salt with various cations, the free base or its acid addition salt and said salt converted to other pharmaceutically acceptable salts by conventional salt exchange techniques, e.g., by mixing equimolar proportions of solutions of appropriate acid and base and removing the solvent or by ion-exchange chromatography.

The glycines of formula (II) prepared by route (2) or (3) above exist in D- and L-optically active forms. The L-form is the preferred form, the D-form being substantially inactive. It will therefore by appreciated that the invention includes the L- and DL-forms and the compounds of the invention derived from L-glycines will be substantially more active than those derived from the racemic (DL) form.

The compounds of the invention may be administered to patients in admixture with or dissolved in a pharmaceutically acceptable diluent or carrier selected with regard to the intended route of administration and standard pharmaceutical practice.

The compounds may be administered parenterally, for example by intramuscular, intravenous or subcutaneous injection. For parenteral administration, they are best used in the form of a sterile aqueous solution which may be contain other solutes, for example enough salts (e.g., sodium acetate, sodium lactate, sodium citrate, sodium succinate or sodium chloride) or dextrose to make the solution isotonic with blood.

For administration to human patients, it is expected that the daily dosage level of a compound of the formula (I) or the L- form of a compound of the formula (II) will be from 1 to 10, preferably 2-5 mg./kg. per day, for a typical (70 kg.) adult patient. Thus, dosage units for parenteral administration can be expected to contain from 70-700 mg. of the active compound. A typical vial could be a 50 ml. vial containing 70-700 mg. of the active compound in 30-50 ml. of solution. The racemic (DL) form of a compound of formula (II) will of course have to be used at approximately twice the levels used for the L-form of the same compound.

It should of course be appreciated that, in any event, the physician will determine the actual dosage which will be most suitable for the individual and it will vary with the age, weight and response of the particular patient and the route of administration. The above average dosages are exemplary of the average patient; there may, of course, be individual cases where higher or lower dosage ranges are merited.

The potential activity of the compounds of the formula (I) and (II) in treating diseases characterized by reduced blood flow, reduced oxygen availability or reduced carbohydrate metabolism in the cardiovascular system, is assessed by virtue of their abilities to;

(1) increase the oxidation of glucose and/or pyruvate by isolated rat muscle preparations in vitro;

(2) increase the proportion of the active form of the enzyme pyruvate dehydrogenase (PDH) in organs of animals (e.g., rat heart) in vivo; and (3) reduce oxygen demand and affect the relative utilization of carbohydrate and lipid metabolites by the electrically-paced heart of an anaesthetised dog in the presence or absence of an isoprenaline stimulus.

Activity in these tests is indicative of the potential utility of the compounds in the treatment of ischaemic heart disease and cardiac failure.

The compounds of formulae (I) and (II) have been tested for their ability to increase the oxidation of glucose and/or pyruvate as follows:

Diaphragm tissue is obtained from rats fed on a high fat diet similar to 'Diet B' described by Zaragoza and Felber, Horm. Metab. Res., 2, 323 (1970). Pyruvate oxidation by such tissue is assessed by measurement of the rate of incorporation of carbon-14 from carbon-14-labelled pyruvate into carbon dioxide in vitro, as described by Bringold, Eur. J. Biochem., 26, 360 (1972). The rate of pyruvate oxidation is depressed by 50–75% compared with that by diaphragm tissue from rats fed on a normal diet. When the compounds of the invention are added to the medium, they are found to stimulate pyruvate oxidation by diaphragm tissue from fat-fed rats in a dose dependent manner.

The degree of stimulation at the concentration indicated is shown in the following table:

| Example | Concentration, m. mol. | % Stimulation |
| --- | --- | --- |
| 2 | 1 | 105 |
| 3 | 1 | 128 |
| 4 | 0.5 | 69 |
| 6 | 0.5 | 29 |
| 7 | 0.5 | 23 |
| 8 | 0.5 | 95 |
| 9 | 0.5 | 42 |
| 10 | 0.5 | 46 |
| 11 | 2 | 99 |
| 12 | 0.5 | 58 |
| 13 | 0.5 | 21 |
| 15 | 2 | 11 |

The rate of glucose oxidation by isolated hearts from starved rats is measured in a recirculating oxygenated perfusion system, by measuring the rate of incorporation of carbon-14 from carbon-14-labelled glucose into carbon dioxide using a method similar to those described by Morgan et al., J. Biol. Chem. 236, 253 (1961) and by Randle et al., Biochem. J., 93, 652 (1964).

The ability of the compounds of this invention to increase the proportion of the active form of the pyruvate dehydrogenase enzyme has been measured in the following test:

Rats fed on a high fat diet as in the previous test, are treated either with placebo or with the compound of formula (I) or (II) by sub-cutaneous or intravenous injection or by oral administration. After 1½ hours the rat hearts are removed and homogenized under conditions which minimize changes in the proportion of the pyruvate dehydrogenase enzyme (PDH) which is present in the active form, as described by Whitehouse and Randle, Biochem, J., 134, 651 (1973). The total amount of the enzyme present (PDHt) and the amount which is present in the active form (PDHa) are assessed by a method similar to that described by Taylor et al., J. Biol. Chem., 248, 73 (1973). The fat-feeding process is found to depress the ratio PDHa/PDHt from a normal value of about 0.7 to a value in the range from 0.1 to 0.3. Treatment of fat-fed rats with the compounds of formula (I) or (II) parenterally increases this ratio in a dose-dependent manner.

The increase in PDHa/PDHt ration affected by certain of the compounds when administered by subcutaneous infection at the dosage indicated is shown in the following table:

| Example | Placebo | Dosage mmol/kg | PDHa/PDHt ratio |
| --- | --- | --- | --- |
| 2 | 0.27 | 1.2 | 0.48 |
| 3 | 0.11 | 0.3 | 0.21 |
| 6 | 0.12 | 0.6 | 0.46 |
| 7 | 0.12 | 0.6 | 0.47 |
| 11 | 0.20 | 0.3 | 0.26 |
| 12 | 0.12 | 0.3 | 0.36 |

The ability of compounds of formula (I) or (II) to reduce oxygen demand and affect the relative utilization of carbohydrate and lipid metabolites in the heart may be assessed by measuring the effect of the compounds on myocardial blood flow and metabolism in fasted, closed-chest, anaesthetised beagle dogs, with cardiac catheterisation to enable simultaneous sampling of coronary sinus and arterial blood to be carried out. Coronary sinus blood flow is measured by the hydrogen gas clearance technique described by Aukland et al., Circulation Res., 14, 164 (1964). The heart is paced electrically at 155 beats/minute and recordings of haemodynamic parameters (blood pressure, left ventricular pressure and the first derivative of the latter) are made continuously. Control measurements of coronary blood flow are made and samples of blood taken at 40 minute intervals, both in an untreated animal and in the same animal dosed with an infusion of isoprenaline (60 ng./kg./min.), which both stimulates cardiac contraction and increases plasma free fatty acid levels. The compound of the invention is then administered intravenously and measurements are made and samples taken again, 40 minutes and 90 minutes later. The blood samples from the artery and coronary sinus are analysed for oxyhaemoglobin, pyruvate and free fatty acid (FFA) content, differences between those of the arterial and coronary sinus blood, when multiplied by coronary blood flow, being a measure of oxygen consumption, pyruvate up-take and FFA uptake by the myocardium respectively.

The preparation of the compounds of the invention is illustrated in the following Examples:

EXAMPLE 1

Ethyl 2,3-dihydro-5-benzo(b)thienylglyoxylate

Powdered, anhydrous aluminum chloride (7.0 g., 0.052 mole) was added in portions to a stirred mixture of 2,3-dihydrobenzo(b)thiophene (7.0 g., 0.051 mole), ethyl oxalyl chloride (7.0 g., 0.051 mole) and dry 1,2-dichloroethane (70 ml.) at 0°–5° C. The resulting deep red solution was stirred at ambient temperature for two hours and then poured into a stirred mixture of concentrated hydrochloric acid and ice. The organic phase was separated and the aqueous phase extracted with chloroform. Evaporation in vacuo of the dried (MgSO$_4$) organic solutions gave a viscous dark oil which was distilled in vacuo to afford the product (4.1 g.) as a viscous yellow oil, b.p. 160°-170° C./1 mm., which partially solidified on standing overnight.

Use of methyl oxalyl chloride, n-propyl oxalyl bromide or the corresponding isopropyl, isobutyl or n-butyl oxalyl chloride or bromide affords the corresponding methyl, ethyl, propyl or butyl ester of 2,3-dihydro-5-benzo(b)thienylglyoxylate.

EXAMPLE 2

2,3-Dihydro-5-benzo(b)thienylglyoxylic Acid

The product from Example 1 (4.0 g.) was added to a solution of sodium hydroxide (8.8 g., 0.22 mole) in water (120 ml.) and the resulting mixture heated on a steam-bath for one hour. The solution was cooled and washed with diethyl ether; it was then acidified with dilute hydrochloric acid and extracted with diethyl ether. Evaporation of the dried (MgSO$_4$) ether extract gave an oil which was dissolved in warm toluene. The toluene solution was cooled to precipitate the required product (2.0 g.) as yellow crystals, m.p. 122°-123° C.

Analysis %:

Found: C, 57.7; H, 4.1; C$_{10}$H$_8$O$_3$S requires: C, 57.7; H, 3.8.

EXAMPLE 3

2,3-Dihydro-5-benzo(b)furanylglyoxylic Acid

Ethyl 2,3-dihydro-5-benzo(b)furanylglyoxylate was prepared from 2,3-dihydrobenzo(b)furan by reaction with ethyl oxalyl chloride as described in Example 1 and hydrolyzed as described in Example 2 to give the required product, m.p. 139°-141° C.

EXAMPLE 4

6-Chromanylglyoxylic Acid

Ethyl 6-chromanylglyoxylate was prepared from chroman by reaction with ethyl oxalyl chloride as described in Example 1 and hydrolyzed as described in Example 2. The crude product was obtained as a red oil which was triturated with toluene to furnish the required acid as a pink solid, m.p. 119°-121° C.

Analysis %:

Found: C, 63.95; H, 5.0; C$_{11}$H$_{10}$O$_4$ requires: C, 64.1; H, 4.9.

EXAMPLE 5

DL-2-[2,3-Dihydro-5benzo(b)furanyl]glycine Hydrobromide

A. N-Benzyloxycarbonyl-α-hydroxyglycine (10.4 g., 0.046 mole) was added to a stirred mixture of concentrated sulfuric acid (4 ml.) and glacial acetic acid (36 ml.) at 0°-5° C. followed, after five minutes, by the dropwise addition of 2,3-dihydrobenzo(b)furan (5.8 g., 0.048 mole). The reaction mixture was stirred at ambient temperature overnight and the resulting pale mauve emulsion poured into stirred ice and water to afford a gum, which was induced to solidify. The crude product was collected, washed with water, dried in vacuo, and crystallized from a mixture of ethyl acetate and petroleum ether (b.p. 60°-80° C.) to provide Dl-α-benzyloxycarbonylamino-2,3-dihydro-5-benzo(b)furanyl acetic acid (5.3 g.), m.p. 121°-123° C. Recrystallization of a sample raised the m.p. to 125°-126° C.

Analysis %:

Found: C, 66.1; H, 4.8; N, 4.3; C$_{18}$H$_{17}$NO$_5$ requires: C, 66.0; H, 5.2; N, 4.3.

B. The product from Part A (8.0 g., 0.024 mole) was added in portions to a stirred solution of 48% (by weight) hydrogen bromide in glacial acetic acid (40 ml.) and the mixture stirred at ambient temperature for 45 minutes. The resulting solution was poured into stirred diethyl ether (200 ml.) to give a purple gum which, on trituration with dry diethyl ether, provided an off-white solid. The product was collected by filtration, washed with diethyl ether and crystallized from a mixture of ethyl acetate and methanol to yield the desired product (1.0 g.), m.p. ca. 220° C. (decomp.).

Analysis %:

Found: C, 43.4; H, 4.4; N, 5.1; C$_{10}$H$_{11}$NO$_3$.HBr requires: C, 43.8; H, 4.4; N, 5.1.

EXAMPLE 6

DL-α-Amino-2,3-dihydro-5-benzo(b)furanylacetamide

A. Triethylamine (2.1 g., 0.021 mole) was added dropwise to a stirred solution of the product of Example 5, Part A (6.5 g., 0.02 mole) in dry tetrahydrofuran (THF) (50 ml.) at −5° C. After five minutes, isobutyl chloroformate (2.2 g., 0.02 mole) was added dropwise and the resulting suspension stirred for a further ten minutes before the dropwise addition of a saturated solution of ammonia in ethanol (10 ml.). The suspension was stirred at ambient temperature for one hour, then evaporated in vacuo. The residue was partitioned between ethyl acetate and water, then the organic phase separated, dried (MgSO$_4$), and evaporated in vacuo, to give an oil which rapidly crystallized. Recrystallized from ethyl acetate-methanol furnished DL-α-benzyloxycabonylamino-2,3-dihydro-5-benzo(b)furanylacetamide, m.p. 163°-165° C.

Analysis %.

Found: C, 66.2; H, 5.5; N, 8.1; C$_{18}$H$_{18}$N$_2$O$_4$ requires: C, 66.2; H, 5.6; N, 8.6.

B. A solution of the product from Part A (4.3 g., 0.013 mole) in ethanol (150 ml.) was hydrogenated over 10% palladium-on-charcoal (0.5 g.) at 30 p.s.i. (2.1 kg./cm$^2$) and ambient temperature. Filtration, followed by evaporation in vacuo of the filtrate, gave the crude product as a white solid (1.8 g.). Digestion with diethyl ether, filtration, washing with diethyl ether and drying in vacuo, provided the pure glycinamide (1.5 g.), m.p. 155°-159° C.

Analysis %:

Found: C, 62.2; H, 6.4; N, 14.4; C$_{10}$H$_{12}$N$_2$O$_2$ requires: C, 62.5; H, 6.3; N, 14.6.

EXAMPLE 7

DL-N-(2-Methoxyethyl)-α-amino-2,3-dihydro-5-benzo(b)furanylacetamide Hydrochloride A. The general method of Example 6, Part A, was followed but using 2-methoxyethylamine instead of ammonia to give DL-N-(2-methoxyethyl)-α-benzyloxycarbonylamino-2,3-dihydro-5-benzo(b)furanylacetamide, m.p. 90°-110° C.

Analysis %:

Found: C, 65.5; H, 6.3; N, 7.1; C$_{21}$H$_{24}$N$_2$O$_5$ requires: C, 65.6; H, 6.3; N, 7.3.

B. The product from Part A was deprotected as described in Example 6, Part B and the resulting oil was converted to its hydrochloride salt using ethereal hydrogen chloride. Crystallization from a mixture of 2- propanol and diethyl ether afforded the desired amide (1.2 g.), m.p. 186° C. (decomp.).

Analysis %:

Found: C, 54.4; H, 6.7; N, 10.2; $C_{13}H_{18}N_2O_3$ requires: C, 54.5; H, 6.7; N, 9.8.

EXAMPLE 8

5-Benzo(b)furanylglyoxlic Acid

A. Preparation of 5-Cyanobenzo(b)furan:

5-Bromobenzo(b)-furan (19.3 g., 0.098 mole) was added dropwise to a stirred mixture of cuprous cyanide (0.14 mole) and pyridine at 165° C. Heating at 165° C. was continued for 26 hours and the cool reaction mixture was then added to 10% (by weight) aqueous ammonia solution. Toluene (100 ml.) was added and the resulting mixture stirred for 0.5 hours and then filtered. Ether (250 ml.) was added to the filtrate and the organic phase separated and combined with the ether extracts (2×100 ml.) of the aqueous phase. The combined organic solutions were washed in turn with 5% aqueous ammonia (4×100 ml.), water (100 ml.), dilute hydrochloric acid (3×100 ml.) and finally water (100 ml.). Evaporation in vacuo of the dried (MgSO₄) organic solution gave an oil which readily solidified. Purification was effected by column chromatography on silica gel using methylene chloride as eluent. Trituration of the product with hexane provided pure 5-cyanobenzo(b)furan as a white solid (8.2 g), m.p. 85°–87° C.

Analysis %:

Found: C, 75.2; H, 3.5; N, 9.7; $C_9H_5NO$ requires: C, 75.5; H, 3.5; N, 9.8.

B. A solution of dry methyl methylthiomethyl sulphoxide (7.0 g., 0.056 mole) in dry tetrahydrofuran (25 ml.) was added dropwise to a stirred suspension of 50% sodium hydride in oil dispersion (3.0 g., 0.62 mole) in dry tetrahydrofuran (50 ml.) under nitrogen at ambient temperature. This mixture was stirred for 0.5 hours and a solution of 5-cyanobenzo(b)furan (8.0 g., 0.056 mole) in dry tetrahydrofuran (25 ml.) added dropwise. The now reddish suspension was stirred at 50°–60° C. overnight, and the resulting thick suspension cooled and treated dropwise with water (5 ml.). Methylene chloride (100 ml.) was next added, followed by magnesium sulphate, and the mixture filtered. Evaporation of the filtrate in vacuo furnished a brown solid (15 g.), which was triturated with ethyl acetate, collected, washed with ethyl acetate and then hexane and dried, in vacuo, to give 1-amino-1[5-benzo(b)furanyl]-2-methylsulphinyl-2-methylthio-ethylene (12.7 g.) as a cream solid, m.p. 157°–159° C. (decomp.).

Analysis %: Found: C, 53.9; H, 4.9; N, 5.55; $C_{12}H_{13}NO_2S_2$ requires: C, 53.9; H, 4.9; N, 5.2.

C. A mixture of the enamine from Part B (2.7 g., 0.01 mole), cupric chloride dihydrate (1.7 g., 0.01 mole) and ethanol (30 ml.), was stired at ambient temperature for three days. Cupric oxide (1.6 g., 0.02 mole) was then added and stirring continued for a further 20 hours. The resulting mixture was filtered and the solid thus obtained was washed with ethanol. The combined filtrate and washings were evaporated in vacuo and the residue partitioned between diethyl ether and water. The organic phase was separated, dried (MgSO₄) and evaporated in vacuo, to provide a yellow oil (2.2 g.) which, by ¹H-NMR spectroscopy, was shown to be the desired glyoxylic acid ethyl ester contaminated with about 10% of the corresponding thioglyoxylic acid, S-methyl ester.

D. The mixture of esters (2.15 g.) was dissolved in ethanol (15 ml.) and a solution of sodium hydroxide (1.0 g., 0.025 mole) in water (15 ml.) was added. The resulting mixture was heated on a steam bath for 0.5 hours and then evaporated in vacuo. The residue was partitioned between diethyl ether and water, the aqueous phase separated, acidified with dilute hydrochloric acid and extracted with diethyl ether. The ether solution was washed with water, dried (MgSO₄) and evaporated in vacuo to furnish a yellow solid (1.7 g.). The product was further purified by dissolving in dilute sodium hydroxide solution, extracting the solution with diethyl ether, acidifying to pH 5 with dilute hydrochloric acid, extracting again with diethyl ether, further acidifying to pH 1 and finally extracting with diethyl ether. The final ether extract was dried (MgSO₄) and evaporated in vacuo. Trituration of the residue with hexane afforded the desired glyoxylic acid (1.1 g.) as a yellow solid, m.p. 99°–101° C.

Analysis %:

Found: C, 62.7; H, 3.2; $C_{10}H_6O_4$ requires: C, 63.2; H, 3.2.

EXAMPLE 9

DL-2-[5-Benzo(b)furanyl]glycine

A. Acetic anhydride (3.15 g., 0.03 mole) was added dropwise to a stirred mixture of the enamine product of Example 8, Part B (5.4 g., 0.02 mole), pyridine (1.85 g., 0.023 mole) and methylene chloride (20 ml.). The resulting mixture was stirred at ambient temperature for four hours, and then evaporated in vacuo. The orange residue was triturated with water, filtered, washed with water and then diethyl ether and dried over MgSO₄ to afford a cream solid (4.6 g.). Crystallization of a sample from ethyl acetate gave DL-methyl-α-acetamido-α-methylthio-5-benzo(b)furanyl-thiolacetate, m.p. 163°–165° C.

Analysis %:

Found: C, 54.2; H, 4.9; N, 4.3; $C_{14}H_{15}NO_3S_2$ requires: C, 54.3; H, 4.9; N, 4.5.

B. A solution of the product from Part A (4.2 g., 0.014 mole) in methanol, (90 ml.) was added to a solution of potassium carbonate (3.9 g., 0.028 mole) in water (10 ml.); the resulting material was heated under reflux for three hours, and evaporated in vacuo. The residue was partitioned between diethyl ether and water, and the aqueous phase separated and acidified with dilute hydrochloric acid. The oil which separated, rapidly solidified. This solid was collected, washed with water and dried in vacuo, affording the desired DL-α-acetamido-5-benzo(b)-furanyl acetic acid (2.45 g.) as a white solid, m.p. 230°—232° C.

Analysis %:

Found: C, 61.35; H, 4.7; N, 5.6; $C_{12}H_{11}NO_4$ requires; C, 61.8; H, 4.75; N, 6.0.

C. The above product (2.35 g., 0.01 mole) was added to a solution of sodium hydroxide (1.6 g., 0.04 mole) in water (16 ml.), and the resulting mixture heated under reflux for six hours, cooled and filtered. The filtrate was acidified to pH 5–6 with dilute hydrochloric acid, and the precipitate collected, washed with water and methanol and dried at 120° C. in vacuo, to provide the glycine (1.7 g.) as a white solid, m.p. 260°–261° C. (decomp.).

Analysis %:

Found: C, 62.7; H, 4.7; N, 7.15; $C_{10}H_9NO_3$ requires: C, 62.8; H, 4.75; N, 7.3.

EXAMPLE 10

DL-2-[5-Benzo(b)furanyl]glycinamide

Thionyl chloride (1.95 g., 0.016 mole) was added dropwise to stirred methanol (15 ml.) at $-5°$ to $0°$ C. and the product of Example 9, Part C (2.7 g., 0.014 mole) added in small portions. The resulting solution was stirred at ambient temperature for one hour, heated under reflux for one hour, and evaporated in vacuo. The residue was stirred with concentrated aqueous ammonia solution until the initial oil gave way to a solid, which was collected, washed with water and dried in vacuo. The off-white solid (2.0 g.) was crystallized from water (containing a little decolorising charcoal) to give the crude glycinamide as a white solid (0.90 g.). Further purification was effected by partitioning the product between 5% aqueous sodium bicarbonate solution and ethyl acetate. The organic phase was separated, washed with water, dried (MgSO$_4$) and evaporated in vacuo. The residue was dissolved in hot ethyl acetate and excess hexane added to precipitate the glycinamide (0.63 g.), m.p. 139°–140° C.

Analysis %:
Found: C, 62.7; H, 5.4; N, 14.5; $C_{10}H_{10}N_2O_2$ requires: C, 63.15; H, 5.3; N, 14.7.

EXAMPLE 11

2-Phenyl-5-benzo(b)furanyl Glyoxylic Acid

A. Preparation of 2-phenyl-5-cyanobenzo(b)furan

Potassium tertiary butoxide (11.8 g., 0.105 mole) was added in portions to a stirred solution of acetophenone oxime (13.5 g., 0.1 mole) in dry dimethyl sulphoxide (180 ml.) under nitrogen. The resulting solution was stirred for 0.5 hours, and a solution of 4-fluorobenzonitrile (12.1 g., 0.1 mole) in dry dimethyl sulphoxide (20 ml.) was then added dropwise. The reaction mixture was heated at 50°–60° C. for one hour, then poured into stirred ice-water to give a yellow solid which was collected, washed with water and dried in vacuo. Crystallization from 2-propanol, followed by recrystallization from ethanol, afforded 4-(α-methylbenzylidineaminoxy)benzonitrile (12.3 g.). Further recrystallization of a sample (1.5 g.) from ethanol yielded the pure oxime (1.1 g.), m.p. 110°–111° C. A stirred mixture of the oxime (30.0 g., 0.127 mole) and a saturated solution of hydrogen chloride in glacial acetic acid (210 ml.) was heated on a steam bath for 18 hours. The resulting dark brown solution was filtered hot and the filtrate evaporated in vacuo; as much acetic acid as possible was removed from the residue by azeotroping with toluene. Crystallization from ethanol provided 2-phenyl-5-cyanobenzo(b)-furan (20.0 g.), m.p. 138°–141° C. A sample (2.0 g.) was recrystallized from methanol to afford the pure nitrile (1.4 g.), m.p. 143°–145° C.

Analysis %:
Found: C, 81.9; H, 4.1; N, 6.1; $C_{15}H_{19}NO$ requires: C, 82.2; H, 4.1; N, 6.4.

B. The nitrile from Part A (17.7 g., 0.08 mole) was treated with methyl methylthiomethyl sulphoxide as described in Example 8, Part B. After the addition of water, the thick suspension was diluted with diethyl ether and filtered. Crystallization of the resulting solid from methanol gave 1-amino-1-[2-phenyl-5-benzo(b)-furyl]-2-methylsulphinyl-2-methylthioethylene (16.6 g.); recrystallization of a sample (1.0 g.) from methanol provided the pure enamine (0.7 g.), m.p. 204° C. (decomp.).

Analysis %:
Found: C, 63.1; H, 4.9; N, 3.95; $C_{18}H_{17}NO_2S_2$ requires: C, 62.9; H, 5.0; N, 4.1.

C. A mixture of the enamine from Part B (6.9 g., 0.02 mole), cupric chloride dihydrate (6.8 g., 0.04 mole) and ethanol (140 ml.), was stirred at ambient temperature for 18 hours, and under reflux for 0.75 hours. The resulting solution was cooled and the precipitate collected and recrystallized from ethanol to afford 2-phenyl-5-benzo(b)furanylthioglyoxylic acid, S-methyl ester (2.54 g.), m.p. 124°–126° C.

Analysis %:
Found: C, 68.7; H, 4.1; $C_{17}H_{12}O_3S$ requires: C, 68.9; H, 4.1.

D. A mixture of the S-methyl ester from Part C (4.85 g., 0.016 mole), sodium hydroxide (4.0 g., 0.1 mole), ethanol (50 ml.) and water (100 ml.) was stirred under reflux for 2.5 hours, and allowed to stand at ambient temperature overnight. The precipitate was collected, washed with water and then suspended in water (150 ml.). Acidification of the suspension with dilute hydrochloric acid, followed by diethyl ether extraction and evaporation of the dried (MgSO$_4$) ether extract provided a yellow solid (3.5 g.) which was twice crystallized from toluene to give the pure glyoxylic acid (2.65 g.), m.p. 164°–165° C.

Analysis %:
Found: C, 72.1; H, 3.75; $C_{16}H_{10}O_4$ requires: C, 72.2; H, 3.8.

EXAMPLE 12

2-Methyl-5-benzo(b)furanylglyoxylic Acid

A. 2-Methyl-5-cyanobenzo(b)furan (17.25 g., 0.11 mole) was treated with methyl methylthiomethyl sulphoxide as described in Example 8, Part B, to yield 1-amino-1-[2-methyl-5-benzo(b)furanyl]-2-methylsulphinyl-2-methylthioethylene (12.4 g.), m.p. 185°–186° C.

Analysis %:
Found: C, 55.3; H, 5.3; N, 5.0; $C_{13}H_{15}NO_2S_2$ requires: C, 55.5; H, 5.4; N, 5.0.

B. A mixture of the enamine product from Part A (10.6 g., 0.038 mole), cupric chloride dihydrate (6.45 g., 0.038 mole) and ethanol (140 ml.) was stirred at ambient temperature for 18 hours. The resulting suspension was filtered and the filtrate evaporated in vacuo. The residue was partitioned between diethyl ether and water and, after filtration, the ether phase was separated and combined with a further ether extract of the aqueous phase. Evaporation in vacuo of the dried (Na$_2$SO$_4$), combined ether extracts gave a brown oil (8.1 g.) which, by $^1$H-NMR spectroscopy was shown to be a mixture of the glyoxylic acid ethyl ester and the corresponding thioglyoxylic acid, S-methyl ester.

C. The mixture of esters (8.0 g.) was combined with sodium hydroxide (8.0 g., 0.2 mole), water (50 ml.) and ethanol (50 ml.), and the resulting mixture heated on a steam bath for three hours. The bulk of the ethanol was removed by evaporation in vacuo, and the residual mixture washed with diethyl ether. The aqueous phase was acidified with dilute hydrochloric acid to give a dark reddish oil which was extracted into diethyl ether. Evaporation in vacuo of the dried (Na$_2$SO$_4$) ether extract furnished a red oil which was induced to solidify by addition of petroleum ether (b.p. 40°–60° C.) and scratching. Two crystallizations from toluene provided the desired glyoxylic acid (2.05 g.), m.p. 87°–89° C.

Analysis %:

Found: C, 64.6; H, 4.3; $C_{11}H_8O_4$ requires: C, 64.7; H, 3.95.

EXAMPLE 13

DL-2-[2,3-Dihydro-5-benzo(b)thienyl]glycine

A. N-Chloroacetyl-α-hydroxyglycine (6.5 g., 0.038 mole) was added to a cold, stirred mixture of concentrated sulphuric acid (1.5 ml.) and glacial acetic acid (15 ml.) followed, after five minutes, by the dropwise addition of 2,3-dihydrobenzo(b)thiophen (98%, 4.1 g., 0.03 mole). The reaction mixture was stirred at ambient temperature for five hours, then water (75 ml.) was added to the resulting suspension and the mixture thoroughly stirred. Filtration gave a solid which was washed successively with water, diethyl ether and hexane, then dried, to afford DL-α-chloroacetamido-2,3-dihydro-5-benzo(b)thienylacetic acid (5.6 g.), m.p. 173°–175° C.

Analysis %:
Found: C, 50.36; H, 4.34; N, 4.89; Calculated for $C_{12}H_{12}ClNO_3S$: C, 50.44; H, 4.23; N, 4.90. B.

The product from Part A, above (18.5 g., 0.065 mole) was added to a solution of sodium hydroxide (10.5 g., 0.263 mole) in water (100 ml.) and the resulting mixture was stirred under reflux for 4 hours, then filtered. The pH of the filtrate was adjusted to 6 with concentrated hydrochloric acid; cooling, followed by filtration, gave a solid which was washed successively with water, methanol and diethyl ether and dried. The crude product (7.24 g.) was added to 6 M hydrochloric acid and the resulting suspension stirred at ambient temperature for 18 hours. Filtration, followed by adjustment of the pH of the filtrate to 5–6 with aqueous ammonia solution, gave a precipitate which was washed with water and dried, to give DL-2-[2,3-dihydro-5-benzo(b)thienyl]glycine (6.76 g.), m.p. 236°–238° C. (decomp.).

Analysis %:
Found: C, 56.96; H, 5.50; N, 6.74; Calculated for $C_{10}H_{11}NO_2S$: C, 57.39; H, 5.30; N, 6.69.

EXAMPLE 14

DL-Methyl-2-[2,3-dihydro-5-benzo(b)thienyl]-glycinate Hydrochloride

Thionyl chloride (2.4 ml., 0.033 mole) was added dropwise to stirred methanol (30 ml.) at <10° C. followed by the amino acid (Example 13) (5.6 g., 0.027 mole) in small portions. The reaction mixture was stirred at ambient temperature for one hour, then under reflux for one hour. The hot solution was treated with charcoal, filtered and the filtrate evaporated in vacuo to give a buff solid. The crude hydrochloride salt was purified by dissolving in water, filtering the solution, adjusting the pH to ca. 9 with aqueous ammonia solution and extracting the amino ester with diethyl ether. Evaporation in vacuo of the dried (MgSO4) ether extract furnished the amino ester as an oil (5.18 g.).

A sample of the amino ester (2.0 g.) was dissolved in methanol (10 ml.) and converted to the pure hydrochloride salt using dry etheral hydrogen chloride. Filtration, washing with ether, and drying, provided the required compound as a pale buff solid (2.04 g.), m.p. 199°–201° C. (decomp.).

Analysis %:
Found: C, 50.96; H, 5.46; N, 5.32; Calculated for $C_{11}H_{13}NO_2S_{HCl}$: C, 50.86; H, 5.43; N, 5.39.

EXAMPLE 15

DL-2-[2,3-Dihydro-5-benzo(b)thienyl]glycinamide

A mixture of the amino ester (Example 14) (3.1 g., 0.014 mole) and 0.880 sp. gr. ammonia solution (25 ml.) was stirred at ambient temperature for 20 hours, then filtered to give a solid which was washed with water and dried to provide the crude amide (2.47 g.) as a buff solid. This solid was extracted with boiling methanol (100 ml.), the extract evaporated in vacuo and the residue crystallized from methanol containing charcoal to afford the pure amino amide (0.71 g.) as a white solid, m.p. 193°–195° C.

Analysis %:
Found: C, 57.43; H, 5.81; N, 13.17; $C_{10}H_{12}N_2OS$ requires: C, 57.66; H, 5.81; N, 13.45.

EXAMPLE 16

Employing the appropriate 2,3-dihydrobenzo(b)furan, 2,3-dihydrobenzo(b)thiophene, chroman or thiachroman of the formula (III), the indicated esters are obtained by the procedures of Examples 1 and 4.

$$R^1-(CH_2)_n-X-\text{(phenyl)} + ClCOCO_2R^3 \longrightarrow$$

(III)

$$R^1-(CH_2)_n-X-\text{(phenyl)}-COCO_2R^2$$

| n | X | R¹ | R² |
|---|---|-----|------|
| 0 | S | H | CH₃ |
| 0 | S | 2-CH₃ | C₂H₅ |
| 0 | S | 3-C₆H₅ | n-C₃H₇ |
| 0 | S | 2-(CH₃)₂CH | (CH₃)₂CH |
| 0 | S | 2-(4-HOC₆H₄) | n-C₄H₉ |
| 0 | S | 2-(CH₃)₂CHCH₂ | CH₃ |
| 0 | O | H | CH₃ |
| 0 | O | 2-CH₃ | C₂H₅ |
| 0 | O | 2-C₂H₅ | C₂H₅ |
| 0 | O | 3-(CH₃)₂CH | n-C₃H₇ |
| 0 | O | 2-n-C₄H₉ | CH₃ |
| 0 | O | 2-CH₃CH₂CH(CH₃) | (CH₃)₂CH |
| 0 | O | 3-n-C₃H₇ | t-C₄H₉ |
| 0 | O | 3-(4-CH₃OC₆H₄) | C₂H₅ |
| 0 | O | 2-(2-ClC₆H₄) | C₂H₅ |
| 0 | O | 2-(3-BrC₆H₄) | CH₃ |
| 0 | O | 2-(2-CH₃C₆H₄) | CH₃ |
| 0 | O | 3-(4-FC₆H₄) | CH₃ |
| 0 | O | 2-(2,4-Cl₂C₆H₃) | C₂H₅ |
| 0 | O | 2-(3-Cl,4-HOC₆H₃) | C₂H₅ |
| 0 | O | 3-(3-Br,4-CH₃OC₆H₃) | n-C₄H₉ |
| 1 | S | H | (CH₃)₂CH |
| 1 | S | 4-CH₃ | CH₃ |
| 1 | S | 2-CH₃ | n-C₄H₉ |
| 1 | S | 3-C₂H₅ | n-C₃H₇ |
| 1 | S | 4-(CH₃)₂CHCH₂ | C₂H₅ |
| 1 | S | 2-(CH₃)₂CH | (CH₃)₂CH |
| 1 | S | 4-C₆H₅ | C₂H₅ |
| 1 | S | 2-(3-HOC₆H₄) | C₂H₅ |
| 1 | S | 4-(4-IC₆H₄) | i-C₄H₉ |
| 1 | S | 3-(2-FC₆H₄) | t-C₄H₉ |
| 1 | S | 4-(4-ClC₆H₄) | C₂H₅ |
| 1 | S | 4-(4-CH₃OC₆H₄) | C₂H₅ |
| 1 | O | 4-(4-CH₃C₆H₄) | C₂H₅ |
| 1 | O | H | n-C₃H₇ |
| 1 | O | 3-CH₃ | C₂H₅ |
| 1 | O | 4-(CH₃)₂CH | CH₃ |
| 1 | O | 2-n-C₄H₉ | n-C₄H₉ |
| 1 | O | 4-(CH₃)₂CHCH₂ | C₂H₅ |

-continued

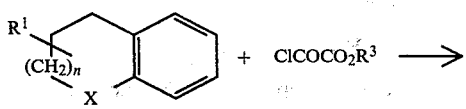

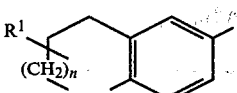

| n | X | R¹ | R² |
|---|---|---|---|
| 1 | O | 4-C₆H₅ | C₂H₅ |
| 1 | O | 4-(4-HOC₆H₄) | C₂H₅ |
| 1 | O | 4-(4-CH₃C₆H₄) | (CH₃)₂CH |
| 1 | O | 2-(3-CH₃OC₆H₄) | C₂H₅ |
| 1 | O | 4-(2-FC₆H₄) | C₂H₅ |
| 1 | O | 4-(3,5-Cl₂C₆H₃) | C₂H₅ |
| 1 | O | 4-(3-BrC₆H₄) | C₂H₅ |
| 1 | O | 4-(4-IC₆H₄) | C₂H₅ |
| 1 | O | 4-(4-n-C₄H₉OC₆H₄) | C₂H₅ |
| 1 | O | 2-(3-C₂H₅OC₆H₄) | CH₃ |
| 1 | O | 4-(2-i-C₄H₉C₆H₄) | C₂H₅ |
| 1 | O | 4-(4-(CH₃)₂CHC₆H₄) | C₂H₅ |

Hydrolysis of the above esters by the procedure of Example 2 provides the corresponding glyoxylic acids of the above formula wherein R² is hydrogen.

EXAMPLE 17

DL-Amino acids of the formula below wherein R² is hydrogen are prepared from the appropriately substituted 2,3-dihydrobenzofuran or chroman by reaction with N-protected hydroxyglycine by the procedure of Example 5. The esters are obtained by using the appropriate alcohol, R²OH, in place of methanol in the procedure of Example 14.

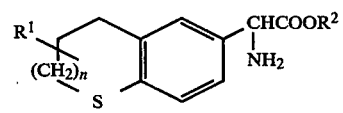

| n | R¹ | R² |
|---|---|---|
| 0 | H | (CH₃)₂CH |
| 0 | 2-CH₃ | C₂H₅ |
| 0 | 2-(CH₃)₂CH | n-C₄H₉ |
| 0 | 3-n-C₄H₉ | CH₃ |
| 0 | 2-CH₃CH₂CH(CH₃) | (CH₃)₂CHCH₂ |
| 0 | 3-n-C₃H₇ | CH₃CH₂CH(CH₃) |
| 0 | 3-(4-CH₃OC₆H₄) | C₂H₅ |
| 0 | 2-C₆H₅ | CH₃ |
| 0 | 3-(3-HOC₆H₄) | C₂H₅ |
| 0 | 2-(4-ClC₆H₄) | (CH₃)₂CH |
| 0 | 2-(4-IC₆H₄) | n-C₄H₉ |
| 0 | 3-(4-CH₃C₆H₄) | CH₃ |
| 0 | 2-(4-n-C₄H₉C₆H₄) | C₂H₅ |
| 0 | 2-(4-n-C₄H₉OC₆H₄) | C₂H₅ |
| 0 | H | n-C₃H₇ |
| 0 | H | i-C₄H₉ |
| 0 | 2-[3,5-(t-C₄H₉)₂C₆H₃] | C₂H₅ |
| 0 | 3-(2-Cl—4-n-C₄H₉OC₆H₃) | CH₃ |
| 1 | 2-CH₃ | CH₃ |
| 1 | 4-CH₃ | C₂H₅ |
| 1 | 3-C₂H₅ | n-C₃H₉ |
| 1 | 4-n-C₄H₉ | (CH₃)₂CH |
| 1 | 2-C₆H₅ | C₂H₅ |
| 1 | 4-(3-HOC₆H₄) | n-C₄H₉ |
| 1 | 4-(4-CH₃C₆H₄) | C₂H₅ |
| 1 | 2-(4-CH₃OC₆H₄) | C₂H₅ |
| 1 | 4-(4-FC₆H₄) | CH₃ |
| 1 | 4-(2-BrC₆H₄) | CH₃ |

-continued

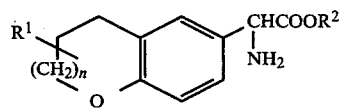

| n | R¹ | R² |
|---|---|---|
| 1 | 2-(4-t-C₄H₉C₆H₄) | CH₃ |
| 1 | 4-(4-n-C₃H₇OC₆H₄) | C₂H₅ |
| 1 | 4-C₆H₅ | C₂H₅ |
| 1 | H | n-C₄H₉ |
| 1 | H | (CH₃)₂CH |
| 1 | 2-[3,4-(HO)₂C₆H₃] | C₂H₅ |
| 1 | 3-(2,4-Br₂C₆H₃) | i-C₃H₇ |
| 1 | 4-(4-CH₃—3-BrC₆H₃) | C₂H₅ |

EXAMPLE 18

Employing the appropriate 2,3-dihydrobenzo(b)thiophene or thiachroman as starting material, the corresponding sulfur-containing amino acids of the formula below wherein R² is hydrogen, R¹ and n are as defined in Example 17 are prepared by the procedure of Example 13. The acids are esterified by the procedure of Example 14 employing the appropriate alcohol to provide esters of the formula below wherein R¹, R² and n are as defined in Example 17.

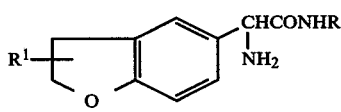

EXAMPLE 19

Employing the appropriate R¹-substituted-α-benzyloxycarbonylamino-2,3-dihydro-5-benzo(b)furanyl acetic acid, obtained by the procedure of Example 5, Part A, and ammonia or amine of formula R³NH₂ as starting materials, the following amides are obtained by the procedures of Examples 6 and 7. For those cases wherein R³ is a benzyl group, the method of Example 15 is employed.

| R¹ | R³ |
|---|---|
| H | CH₃ |
| H | n-C₄H₉ |
| H | (CH₃)₂CH |
| H | (CH₂)₃—OCH₃ |
| H | CH₂CH—CH₂CH₃<br>\|<br>O—n-C₄H₉ |
| H | CH₂CH₂OCH₂CH₃ |
| H | C₆H₅CH₂ |
| H | 4-HOC₆H₄CH₂ |
| 2-CH₃ | 3,4-(CH₃)₂C₆H₃CH₂ |
| 2-n-C₄H₉ | 2-FC₆H₄CH₂ |
| 3-n-C₃H₇ | 4-ClC₆H₄CH₂ |
| 3-C₂H₅ | 3-BrC₆H₄CH₂ |
| 2-CH₃ | CH₂CH₂OCH₃ |
| 2-C₆H₅ | (CH₂)₄O(CH₂)₃CH₃ |
| 2-(4-HOC₆H₄) | C₂H₅ |
| 3-(4-BrC₆H₄) | H |

-continued $$R^1\underset{O}{\overset{}{\boxed{\phantom{xxx}}}}\underset{}{\overset{CHCONHR^3}{\underset{NH_2}{\boxed{\phantom{xxx}}}}}$$

| $R^1$ | $R^3$ |
|---|---|
| 3-(3-FC$_6$H$_4$) | CH$_3$ |
| 2-(4-IC$_6$H$_4$) | CH(CH$_3$)$_2$ |
| 3-(3,4-Cl$_2$C$_6$H$_3$) | CH$_2$CH$_2$OCH$_3$ |
| 2-(3-Cl—4-HOC$_6$H$_3$) | 4-CH$_3$OC$_6$H$_4$CH$_2$ |
| 3-(2-F—4-ClC$_6$H$_3$) | C$_6$H$_5$CH$_2$ |
| 2-(CH$_3$)$_2$CH | CH$_2$OCH$_3$ |
| 3-(CH$_3$)$_2$CHCH$_2$ | CH$_2$O(CH$_2$)$_3$CH$_3$ |
| H | CH$_2$CH(CH$_3$)OC$_2$H$_5$ |
| 2-CH$_3$ | CH$_2$CH(C$_2$H$_5$)OCH$_3$ |
| 2-C$_6$H$_5$ | 4-CH$_3$OC$_6$H$_4$CH$_2$ |
| H | 4-n-C$_4$H$_9$OC$_6$H$_4$CH$_2$ |
| H | 2,4-(i-C$_4$H$_9$)$_2$C$_6$H$_3$CH$_2$ |
| H | 2,4-Cl$_2$C$_6$H$_3$CH$_2$ |
| 3-CH$_3$ | 3-Cl,4-HOC$_6$H$_3$CH$_2$ |

EXAMPLE 20

Similarly, when an alpha-benzyloxycarbonylamino-6-chromanyl acetic acid is employed in the procedure of Examples 6 and 7, or one of the alpha-amino esters provided in Example 17 is reacted with ammonia or an amine, $R^3NH_2$, by the procedure of Example 15, the following compounds are obtained.

$$R^1\underset{O}{\overset{}{\boxed{\phantom{xxx}}}}\underset{}{\overset{CHCONHR^3}{\underset{NH_2}{\boxed{\phantom{xxx}}}}}$$

| $R^1$ | $R^3$ |
|---|---|
| H | t-C$_4$H$_9$ |
| H | CH(CH$_3$)$_2$ |
| H | CH$_2$CH$_2$OCH$_3$ |
| H | (CH$_2$)$_4$OCH$_2$CH$_3$ |
| 4-CH$_3$ | CH$_2$C$_6$H$_5$ |
| 4-(CH$_3$)$_2$CH | CH$_2$O(CH$_2$)$_3$CH$_3$ |
| 4-n-C$_4$H$_9$ | (CH$_2$)$_3$OCH(CH$_3$)$_2$ |
| 4-C$_6$H$_5$ | 4-ClC$_6$H$_4$CH$_2$ |
| 3-(4-HOC$_6$H$_4$) | H |
| 2-(4-n-C$_4$H$_9$C$_6$H$_4$) | CH$_3$ |
| 4-(4-n-C$_4$H$_9$OC$_6$H$_4$) | CH$_2$CH$_2$OCH$_2$CH$_3$ |
| 4-(4-FC$_6$H$_4$) | 3-Cl,—4-HOC$_6$H$_3$CH$_2$ |
| 4-(2,4-Cl$_2$C$_6$H$_3$) | (CH$_3$)$_2$CHCH$_2$ |
| 2-C$_2$H$_5$ | C$_2$H$_5$ |
| H | 3-BrC$_6$H$_4$CH$_2$ |
| H | 4-IC$_6$H$_4$CH$_2$ |

EXAMPLE 21

The alpha-aminoacetamide derivatives of 2,3-dihydrobenzo(b)thiophene and thiachroman of the formula below are prepared by reaction of one of the corresponding amino esters provided in Example 18 or the corresponding amino acid chlorides, with ammonia or an amine of formula $R^3NH_2$ in the procedures of Examples 10 and 15.

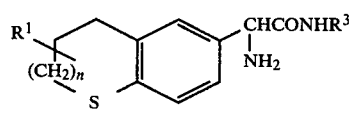

where n and $R^1$ are as given in Example 17 and $R^3$ is as defined in Example 20.

EXAMPLE 22

Employing the appropriate $R^1$-substituted-5-cyanobenzo(b)furan as starting material in the procedures of Examples 8, 11 and 12 provides the following compounds.

$$R^1\underset{O}{\overset{}{\boxed{\phantom{xxx}}}}\underset{}{\overset{COCO_2H}{\boxed{\phantom{xxx}}}}$$

| $R^1$ |
|---|
| 3-CH$_3$ |
| 2-C$_2$H$_5$ |
| 2-n-C$_4$H$_9$ |
| 3-(CH$_3$)$_2$CH |
| 2-(CH$_3$)$_3$C |
| 3-C$_6$H$_5$ |
| 3-(4-BrC$_6$H$_4$) |
| 2-(4-CH$_3$OC$_6$H$_4$) |
| 2-(3-HOC$_6$H$_4$) |
| 2-(4-FC$_6$H$_4$) |
| 2-(4-IC$_6$H$_4$) |
| 3-(4-Cl,2-CH$_3$C$_6$H$_3$) |
| 2-(4-t-C$_4$H$_9$C$_6$H$_4$) |

EXAMPLE 23

In like manner the corresponding benzo(b)thienylglyoxylic acids are prepared from the appropriate $R^1$-substituted-5-cyano-benzo(b)thiophene by the procedures of Examples 8, 11 and 12.

$$R^1\underset{S}{\overset{}{\boxed{\phantom{xxx}}}}\underset{}{\overset{COCO_2H}{\boxed{\phantom{xxx}}}}$$

| $R^1$ |
|---|
| H |
| 2-CH$_3$ |
| 3-CH$_3$ |
| 2-(CH$_3$)$_2$CH |
| 3-n-C$_3$H$_7$ |
| 2-n-C$_4$H$_9$ |
| 2-C$_6$H$_5$ |
| 3-C$_6$H$_5$ |
| 2-(4-BrC$_6$H$_4$) |
| 3-(4-CH$_3$OC$_6$H$_4$) |
| 2-(3-n-C$_4$H$_9$OC$_6$H$_4$) |
| 2-[4-(CH$_3$)$_2$CHC$_6$H$_4$] |
| 3-(4-ClC$_6$H$_4$) |
| 2-(3,4-Cl$_2$C$_6$H$_3$) |

EXAMPLE 24

Similarly, $R^1$-substituted-6-cyano-2H-1-benzopyrans and $R^1$-substituted-6-cyano-2H-1-benzothiapyrans afford the following compounds by the procedures of Examples 8, 11 and 12.

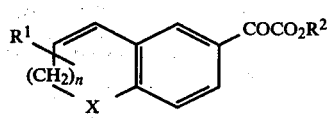

| X | R¹ |
|---|---|
| O | H |
| O | 2-CH$_3$ |
| O | 3-C$_2$H$_5$ |
| O | 4-CH$_3$ |
| O | 4-n-C$_4$H$_9$ |
| O | 3-(CH$_3$)$_2$CHCH$_2$ |
| O | 2-C$_6$H$_5$ |
| O | 3-(4-HOC$_6$H$_4$) |
| O | 4-(4-CH$_3$OC$_6$H$_4$) |
| O | 2-(2-ClC$_6$H$_4$) |
| O | 4-(4-t-C$_4$H$_9$C$_6$H$_4$) |
| O | 4-(3,4-Cl$_2$C$_6$H$_3$) |
| S | H |
| S | 3-CH$_3$ |
| S | 4-CH$_3$ |
| S | 2-n-C$_4$H$_9$ |
| S | 4-C$_2$H$_5$ |
| S | 3-(CH$_3$)$_2$CH |
| S | 3-C$_6$H$_5$ |
| S | 4-(3-CH$_3$C$_6$H$_4$) |
| S | 2-(4-CH$_3$OC$_6$H$_4$) |
| S | 4-(4-FC$_6$H$_4$) |
| S | 3-(3,5-Cl$_2$C$_6$H$_3$) |

EXAMPLE 25

An ethereal solution of diazomethane is added in portions to a solution of 2-methyl-5-benzo(b)furanylglyoxylic acid in dry ethyl ether until the yellow color of diazomethane persists. The resulting mixture is stirred five minutes and a few drops of ethereal acetic acid added to consume the excess reagent. The ether solution is washed with water, dilute sodium bicarbonate solution, water again and dried over anhydrous magnesium sulfate. The ether is evaporated to obtain methyl 2-methyl-5-benzo(b)furanylglyoxylate.

The butyl ester is obtained by transesterification of methyl 2-methyl-5-benzo(b)furanylglyoxylate by dissolving the methyl ester in an large excess of n-butanol containing a catalytic amount of sodium butoxide. The mixture is heated at reflux while distilling off the methanol by means of a Vigreaux column and fractionating head. When the methanol is removed, the butanol solution is neutralized, filtered and evaporated to dryness in vacuo to obtain n-butyl 2-methyl-5-benzo(b)furanylglyoxylate which is purified, if desired, by chromatography on silica gel.

In similar manner the remaining carboxylic acids provided in Examples 22-24 are converted to esters of the formula below where R² is methyl, ethyl, isopropyl, n-propyl, isobutyl or n-butyl.

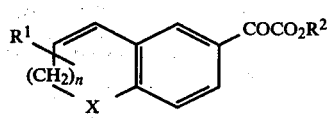

where n, X and R¹ are as defined in Examples 22-24.

EXAMPLE 26

The following racemic compounds are prepared from the appropriate R¹-substituted-5-cyano-benzo(b)furan or R¹-substituted-5-cyano-benzo(b)thiophene by the procedure of Example 9.

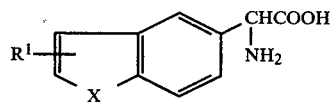

where R¹ and X are as defined in Examples 22 and 23.

EXAMPLE 27

DL-Glycine derivatives of the formula below are likewise prepared from the appropriate R¹-substituted-6-cyano-2H-1-benzopyran or R¹-substituted-6-cyano-2H-1-benzothiapyran by the procedure of Example 9.

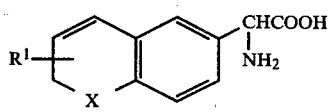

where R¹ and X are as defined in Example 24.

EXAMPLE 28

The amino acids provided in Examples 26 and 27 are converted to the corresponding amino esters and amino ester hydrochloride salts of the formula below by employing the appropriate alcohol, R²OH, in place of methanol in the procedure of Example 14.

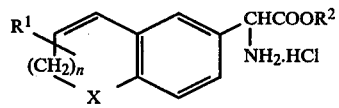

where n, X and R¹ are as defined in Examples 26 and 27 and R² is methyl, ethyl, n-propyl, isopropyl, n-butyl, isobutyl and sec-butyl.

EXAMPLE 29

The amino acids provided in Examples 26 and 27 are converted to acid halides by means of thionyl chloride or thionyl bromide and the acid halide is reacted with ammonia or an amine of formula R³NH$_2$ by the procedure of Example 10 to provide amides of the formula

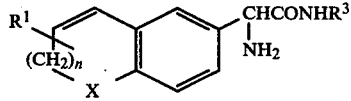

where n, X and R¹ are as defined in Examples 26 and 27 and R³ is as defined in Examples 19 and 20.

EXAMPLE 30

Acid Addition Salts of Amino Acids, Amino Esters and Amino Amides

The method is exemplified as follows: DL-alpha-amino-2,3-dihydro-5-benzo(b)furanyl acetamide is warmed in sufficient ethanol to effect solution. An ethanol solution containing an equimolar amount of anhydrous citric acid is added and the resulting mixture evaporated to dryness and recrystallized to obtain the citrate salt. In like manner the remaining amino acids, amino esters and amino amides of the invention are converted to citrate salts.

When acids such as hydrochloric, hydrobromic, sulfuric, phosphoric, acetic, maleic, fumaric, succinic, lactic, tartaric, gluconic, saccharic, or p-toluenesulfonic acid are employed in place of citric acid in the above procedure, the corresponding acid addition salts are obtained in each case.

EXAMPLE 31

Cationic Salt Formation

DL-2-Methyl-5-benzofuranylglyoxylic acid (0.01 mole) is dissolved in 200 ml. of warm ethanol. An equivalent amount of alcoholic potassium hydroxide is added, the mixture stirred for 15 minutes and cooled. The precipitated potassium salt is recovered by filtration, washed with cold ethanol, ethyl ether and dried. When aqueous sodium hydroxide, aqueous calcium hydroxide or alcoholic solutions of ammonia or amines such as arginine, N-methylglucamine or choline are used in place of potassium hydroxide, the corresponding cationic salts are obtained in like manner.

When DL-2-methyl-5-benzofuranylglycine is employed in place of the above glyoxylic acid in the above procedures, the corresponding cationic salts of this glycine derivative are provided.

When the remaining glyoxylic acid or glycine derivatives of the invention, of formulae (I) wherein $R^2$ is hydrogen or (II) wherein R is OH, are employed in the above procedures, the corresponding cationic salts are obtained in each case.

EXAMPLE 32

Parenteral Solutions

A. Glacial acetic acid (12.0 g.) and sodium acetate anhydrous (16.4 g.) are each dissolved in 1000 ml. of freshly distilled water to produce 0.2 molar solutions. 148.0 ml. of the acetic acid solution is then mixed with 352.0 ml. of the sodium acetate solution and the mixture made up to 1000 ml. with freshly distilled water. 2,3-Dihydro-5-benzo(b)furanylglyoxylic acid, 10 g., is then added and the resulting solution is then sterilized by filtration through a suitable bacteria-proof filter under aseptic conditions into sterile 50 ml. glass vials, which when filled with 30 ml. of the final solution, contain 300 mg. of the active ingredient.

B. Succinic acid (23.62 g.) and sodium hydroxide (98 g.) are each dissolved in 1000 ml. of freshly distilled water to produce 0.2 molar solutions. 250 ml. of the succinic acid solution is then mixed with 267.0 ml. of the sodium hydroxide and the mixture made up to 1000 ml. with freshly distilled water. L- or DL-alpha-amino-2,3-dihydro-5-benzo(b)furanylacetamide, 10 g., is then added and the resulting 1% w/v solution is then sterilized as in Part A, above. Sterile 50 ml. glass vials, when filled with 40 ml. of the final solution, contain 400 mg. of the active ingredient.

PREPARATION A

6-Cyano-4-(3-methylphenyl)-2H-1-benzothiopyran

6-Bromo-4-(3-methylphenyl)-2H-1-benzothiopyran (31.89 g., 0.10 mole) [prepared by addition of 3-methylphenylmagnesium bromide to an ethyl ether solution of 6-bromo-4-thiachromanone and subsequent dehydration of the resulting 6-bromo-4-hydroxy-4-(3-methylphenyl)-3,4-dihydro-2H-1-benzothiopyran] is added dropwise to a stirred mixture of cuprous cyanide (12.5 g., 0.14 mole) and 35 ml. dimethylformamide at 160° C. Heating is continued at 160°–170° C. for six hours. The cooled reaction mixture is added to 100 ml. 10% (by weight) aqueous ammonia. Toluene, 100 ml., is added and the resulting mixture stirred for 30 minutes and filtered. The filtrate is extracted with ethyl ether, the organic layers separated and the combined extracts washed with dilute ammonium hydroxide, water, dilute hydrochloric acid and finally with water again. The extracts are dried ($MgSO_4$) and evaporated to dryness to afford the crude title compound which is purified by column chromatography on silica gel.

PREPARATION B

6-Cyano-3-phenyl-2H-1-benzopyran

A solution of 44.6 g. (0.2 mole) 6-amino-3-phenyl-2H-1-benzopyran in 600 ml. water and 20 ml. concentrated hydrochloric acid is stirred and cooled to 0° C. and held at that temperature while adding 50 ml. concentrated hydrochloric acid and a solution of 14.4 g. sodium nitrite in 60 ml. water. The slight excess of nitrous acid is destroyed with urea. In a separate flask in the hood, a solution of 72.7 g. nickel nitrate in 100 ml. water is added to 250 ml. of a solution containing 81.4 g. potassium cyanide and 20 g. sodium hydroxide. Benzene, 150 ml., is added followed by crushed ice. The diazonium salt solution, prepared above, is added over 30 minutes with vigorous stirring while maintaining the temperature at 0°–5° C. The mixture is allowed to warm to room temperature over two hours, heated to 50° C., cooled and the aqueous layer separated. After extraction with ethyl ether, the extracts are washed with bicarbonate solution, water, saturated brine, and dried over anhydrous magnesium sulfate. The ether is evaporated to provide the title compound which may be purified by column chromatography on silica gel.

PREPARATION C

Employing the procedures of Preparations A and B, the following compounds are prepared from the appropriate starting materials.

| n | X | $R^1$ |
|---|---|-------|
| 0 | O | 3-$CH_3$ |
| 0 | O | 2-$C_2H_5$ |
| 0 | O | 2-n-$C_4H_9$ |
| 0 | O | 3-$(CH_3)_2CH$ |
| 0 | O | 2-$(CH_3)_3C$ |
| 0 | O | 3-$C_6H_5$ |
| 0 | O | 3-(4-Br$C_6H_4$) |
| 0 | O | 2-(4-$CH_3OC_6H_4$) |
| 0 | O | 2-(3-HO$C_6H_4$) |
| 0 | O | 2-(4-F$C_6H_4$) |
| 0 | O | 2-(4-I$C_6H_4$) |
| 0 | O | 3-(4-Cl,2-$CH_3C_6H_3$) |
| 0 | O | 2-(4-t-$C_4H_9C_6H_4$) |
| 0 | S | 2-$CH_3$ |
| 0 | S | 3-$CH_3$ |
| 0 | S | 2-$(CH_3)_2CH$ |
| 0 | S | 3-n-$C_3H_7$ |
| 0 | S | 2-n-$C_4H_9$ |
| 0 | S | 2-$C_6H_5$ |
| 0 | S | 3-$C_6H_5$ |
| 0 | S | 2-(4-Br$C_6H_4$) |
| 0 | S | 3-(4-$CH_3OC_6H_4$) |
| 0 | S | 2-(3-n-$C_4H_9OC_6H_4$) |

-continued

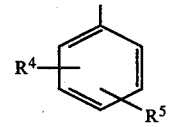

| n | X | R¹ |
|---|---|---|
| 0 | S | 2-[4-(CH₃)₂CHC₆H₄] |
| 0 | S | 3-(4-ClC₆H₄) |
| 0 | S | 2-(3,4-Cl₂C₆H₃) |
| 1 | O | 2-CH₃ |
| 1 | O | 3-C₂H₅ |
| 1 | O | 4-CH₃ |
| 1 | O | 4-n-C₄H₉ |
| 1 | O | 3-(CH₃)₂CHCH₂ |
| 1 | O | 2-C₆H₅ |
| 1 | O | 3-(4-HOC₆H₄) |
| 1 | O | 4-(4-CH₃OC₆H₄) |
| 1 | O | 2-(2-ClC₆H₄) |
| 1 | O | 4-(4-t-C₄H₉C₆H₄) |
| 1 | O | 4-(3,4-Cl₂C₆H₃) |
| 1 | S | H |
| 1 | S | 3-CH₃ |
| 1 | S | 4-CH₃ |
| 1 | S | 2-n-C₄H₉ |
| 1 | S | 4-C₂H₅ |
| 1 | S | 3-(CH₃)₂CH |
| 1 | S | 3-C₆H₅ |
| 1 | S | 4-(3-CH₃C₆H₄) |
| 1 | S | 2-(4-CH₃OC₆H₄) |
| 1 | S | 4-(4-FC₆H₄) |
| 1 | S | 3-(3,5-Cl₂C₆H₃) |

PREPARATION D

5-Cyano-2-methylbenzo(b)furan i. 4-(Isopropylideneaminoxy)benzonitrile.

To a solution of 7.4 g. (0.1 mole) acetone oxime in 150 ml. tetrahydrofuran is added 4.3 g. of a 56% mineral oil dispersion of sodium hydride and the mixture stirred at room temperature until gas evolution is complete. Dimethyl sulfoxide, 50 ml., is added followed by 12.1 g. (0.1 mole) 4-fluorobenzonitrile. The resulting mixture is stirred for two hours at room temperature and poured into water. The product is extracted with ethyl ether, the extracts washed with water and evaporated to dryness. The crude O-aryl oxime is purified by crystallization or chromatography.

ii. 4-(Isopropylideneaminoxy)benzonitrile (3.5 g., 0.02 mole) in 50 ml. 8 N alcoholic hydrogen chloride is heated at reflux for two hours. Addition of water affords a precipitate which is filtered off, dried and recrystallized to afford the title compound.

In similar manner compounds of the formula shown below are obtained from the appropriate starting materials

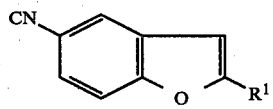

where R¹ is phenyl or substituted phenyl as defined in Preparation C.

We claim:

1. A compound of the formula

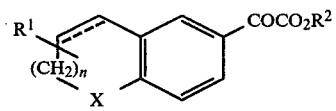

or a pharmaceutically acceptable cationic salt thereof, wherein R¹ is hydrogen, alkyl having from one to four carbon atoms or

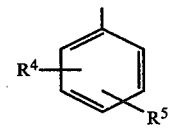

where R⁴ and R⁵ are the same or different and are each a member selected from the group consisting of H, OH, F, Cl, Br, I and alkyl and alkoxy having from one to four carbon atoms;
R² is hydrogen or alkyl having from one to four carbon atoms;
X is oxygen or sulfur;
n is 0 or 1; and the broken line is a bond or no bond; with the proviso that when X is oxygen and the broken line is no bond,
R¹ is

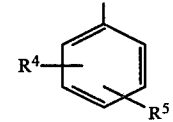

2. A compound according to claim 1 wherein the broken line is a bond.

3. A compound according to claim 1 wherein R¹ is alkyl having from one to four carbon atoms or

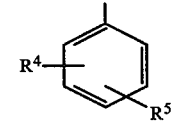

and the broken line is no bond.

4. A compound according to claim 3 wherein R¹ is

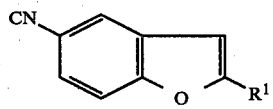

5. A compound according to claim 1 wherein X is oxygen.

6. A compound according to claim 5 wherein n is 0.

7. A compound according to claim 6 wherein the broken line is a bond.

8. A compound according to claim 7 wherein R¹ is phenyl or methyl.

9. The compound according to claim 8 wherein R¹ is 2-phenyl and R² is hydrogen.

10. The compound according to claim 8 wherein $R^1$ is 2-methyl and $R^2$ is hydrogen.

11. A compound according to claim 7 wherein $R^1$ is hydrogen.

12. The compound according to claim 11 wherein $R^2$ is hydrogen.

13. A compound according to claim 1 wherein the broken line is no bond, $R^1$ is hydrogen and X is sulfur.

14. A compound according to claim 13 wherein n is 0.

15. The compound according to claim 14 wherein $R^2$ is hydrogen.

16. An L- or DL-glycine derivative of the formula

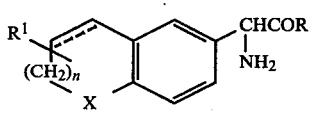

or a pharmaceutically acceptable cationic and acid addition salt thereof wherein R is $OR^2$ or $NHR^3$ where $R^2$ is hydrogen or alkyl having from one to four carbon atoms and $R^3$ is a member selected from the group consisting of hydrogen, alkyl having from one to four carbon atoms, alkoxyalkyl having from one to four carbon atoms in each of the alkyl groups and

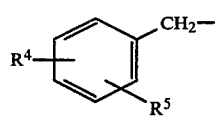

where $R^4$ and $R^5$ are the same or different and are each a member selected from the group consisting of H, OH, F, Cl, Br, I and alkyl and alkoxy having from one to four carbon atoms;

$R^1$ is hydrogen, alkyl having from one to four carbon atoms or

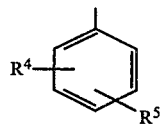

where $R^4$ and $R^5$ are as defined above;

X is oxygen or sulfur;

n is 0 or 1 and the broken line is a bond or no bond; with the proviso that when X is oxygen, n is 0 and the broken line is no bond, R is $NHR^3$.

17. A compound according to claim 16 wherein n is 0.

18. A compound according to claim 17 wherein X is oxygen.

19. A compound according to claim 18 wherein the broken line is no bond.

20. A compound according to claim 19 wherein $R^1$ is hydrogen.

21. A compound according to claim 20 wherein R is $NHR^3$.

22. A compound according to claim 21 wherein $R^3$ is hydrogen or methoxyethyl.

23. The compound according to claim 22: DL-2-amino-2-[2,3-dihydro-5-benzo(b)furanyl]acetamide.

24. The compound according to claim 22: DL-N-(2-methoxymethyl)-2-amino-2-[2,3-dihydro-5-benzo(b)-furanyl]acetamide.

25. A compound according to claim 18 wherein the broken line is a bond.

26. A compound according to claim 25 wherein $R^1$ is hydrogen.

27. The compound according to claim 26 wherein R is OH.

28. The compound according to claim 25 wherein R is $NH_2$.

29. A pharmaceutical composition comprising a pharmaceutically acceptable carrier and a cardiovascular blood flow, oxygen availability or carbohydrate metabolism increasing amount of a compound of claim 1.

30. A pharmaceutical composition comprising a pharmaceutically acceptable carrier and a cardiovascular blood flow, oxygen availability or carbohydrate metabolism increasing amount of a compound of claim 16.

31. A method of treating a mammalian subject suffering from a disease or condition attributable to reduced blood flow, reduced oxygen availability or reduced carbohydrate metabolism in the cardiovascular system which comprises parenterally administering to said subject a cardiovascular blood flow, oxygen availability or carbohydrate metabolism increasing amount of a compound of the formula

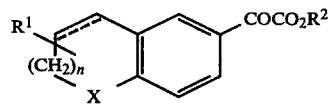

or pharmaceutically acceptable cationic salt thereof, wherein $R^1$ is hydrogen, alkyl having from one to four carbon atoms or

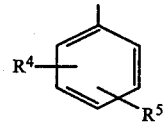

where $R^4$ and $R^5$ are the same or different and are each a member selected from the group consisting of H, OH, F, Cl, Br, I, and alkyl and alkoxy having from one to four carbon atoms;

$R^2$ is hydrogen or alkyl having from one to four carbon atoms;

X is oxygen or sulfur;

n is 0 or 1; and the broken line is a bond or no bond.

32. The method according to claim 31 wherein said compound is 2,3-dihydro-5-benzo(b)furanylglyoxylic acid.

33. The method according to claim 31 wherein said compound is 2,3-dihydro-5-benzo(b)thienylglyoxylic acid.

34. The method according to claim 31 wherein said compound is 6-chromanylglyoxylic acid.

35. The method according to claim 31 wherein said compound is 5-benzo(b)furanylglyoxylic acid.

36. The method according to claim 31 wherein said compound is 2-methyl-5-benzo(b)furanylglyoxylic acid.

37. A method of treating a mammalian subject suffering from a disease or condition attributable to reduced blood flow, reduced oxygen availability or reduced carbohydrate metabolism in the cardiovascular system which comprises parenterally administering to said subject a cardiovascular blood flow, oxygen availability or carbohydrate metabolism increasing amount of an L- or DL-glycine derivative of the formula

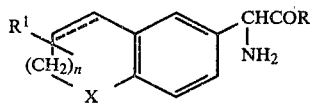

or a pharmaceutically acceptable cationic or acid addition salt thereof wherein

R is $OR^2$ or $NHR^3$ where $R^2$ is hydrogen or alkyl having from one to four carbon atoms and $R^3$ is a member selected from the group consisting of hydrogen, alkyl having from one to four carbon atoms, alkoxyalkyl having from one to four carbon atoms in each of the alkyl groups and

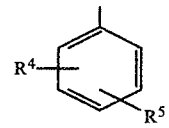

where $R^4$ and $R^5$ are the same or different and are each a member selected from the group consisting of H, OH, F, Cl, Br, I and alkyl and alkoxy having from one to four carbon atoms;

$R^1$ is hydrogen, alkyl having from one to four carbon atoms or where $R^4$ and $R^5$ are as defined above;
X is oxygen or sulfur;
n is 0 or 1 and the broken line is a bond or no bond.

38. The method according to claim 37 wherein said compound is DL-2-amino-2-[2,3-dihydro-5-benzo(b)-furanyl]acetamide.

39. The method according to claim 37 wherein said compound is DL-N-(2-methoxyethyl)-2-amino-2-[2,3-dihydro-5-benzo(b)furanyl]acetamide.

* * * * *

UNITED STATES PATENT AND TRADEMARK OFFICE
CERTIFICATE OF CORRECTION

PATENT NO. : 4,341,792

DATED : July 27, 1982

INVENTOR(S) : Ian T. Barnish et al

It is certified that error appears in the above-identified patent and that said Letters Patent is hereby corrected as shown below:

Column 32, line 2, "methoxymethyl" should read --methoxyethyl--

Signed and Sealed this

First Day of March 1983

[SEAL]

Attest:

GERALD J. MOSSINGHOFF

Attesting Officer    Commissioner of Patents and Trademarks